United States Patent [19]
Lee et al.

[11] Patent Number: 6,024,690
[45] Date of Patent: Feb. 15, 2000

[54] RADIATION SOURCE WITH DELIVERY WIRE

[75] Inventors: Eric J. Lee, Pepper Pike; Urs Hafeli, Cleveland, both of Ohio; Eugene J. Jung, Jr., San Diego, Calif.

[73] Assignee: Endosonics Corporation, Rancho Cordova, Calif.

[21] Appl. No.: 08/886,602

[22] Filed: Jul. 1, 1997

[51] Int. Cl.$^7$ .................................................. A61N 5/00
[52] U.S. Cl. ............................................................ 600/3
[58] Field of Search ............................................ 600/1–8

[56] References Cited

U.S. PATENT DOCUMENTS

| | | |
|---|---|---|
| 5,199,939 | 4/1993 | Dake et al. . |
| 5,213,561 | 5/1993 | Weinstein et al. . |
| 5,302,168 | 4/1994 | Hess . |
| 5,354,257 | 10/1994 | Roubin et al. . |
| 5,411,466 | 5/1995 | Hess . |
| 5,503,613 | 4/1996 | Weinberger . |
| 5,540,659 | 7/1996 | Teirstein . |
| 5,616,114 | 4/1997 | Thornton et al. . |
| 5,624,372 | 4/1997 | Liprie . |
| 5,643,171 | 7/1997 | Bradshaw et al. . |
| 5,688,220 | 11/1997 | Verin et al. . |

FOREIGN PATENT DOCUMENTS

| | | |
|---|---|---|
| 91 02 312 U | 8/1992 | Germany . |
| PCT/US95/12223 | 4/1996 | WIPO . |

OTHER PUBLICATIONS

Verin et al., Intra–arterial Beta Irradiation Prevents Neointimal Hyperplasia in a Hypercholesterolemic Rabbit Restenosis Model, Circulation vol. 92, No. 8 Oct. 15, 1995, pp. 2284–2290.

Verin et al., Feasibility of Intracoronary B–Irradiation to Reduce Restenosis After Balloon Angioplasty, Circulation vol. 95, No. 5, Mar. 4,1997, pp. 1138–1144.

D. Liermann, J. Berkefeld, G. Herrman, B. Schopohl, G. Strassman, I. Adamitz, and J. Kollath. Intervention und Klinik im Zusammenhang mit der endovaskulä Radiatio intimaler Hyperplasien im GefäBsystem. *Radiologe*, 34: 524–533 (1994).

P. S. Teirstein, V. Massullo, S. Jani, R.J. Russo, A. Schatz, S. Steuterman, N. B. Morris, and P. Tripuraneni. Catheter–Based Radiation Therapy To Inhibit Restenosis Following Coronary Stenting. *Circulation*, 92L I–543 (1995).

B. Schopohl, L. Jüling–Pohlit, H. D. Böttcher, D. Liermann, J. Kollath, C. G. Rahl, K. H. Manegold, and U. Ramm. Endovascular Irradiation For Avoidance Or Recurrent Stenosis After Stent Implantation in Peripheral Arteries—5 Years Follow–Up. Proceedings Restenosis Meeting Atlanta, 1: 89–92 (1996).

H. I. Amols, Radioactive Source Design and Dosimetry for Intravascular Brachytherapy Treatment of Restenosis. *Med. Phys.*, vol. 23, No. 6, p. 1119 (1996).

H. I. Amols, L. E. Reinstein, and J. Weinberger, Dosimetry of a Radioactive Coronary Balloon Dilation Catheter for Treatment of Neointimal Hyperplasia. *Med. Phys.*, vol. 23, (10) pp. 1783–1788, (Oct., 1996).

(List continued on next page.)

*Primary Examiner*—John P. Lacyk
*Attorney, Agent, or Firm*—Nydegger & Associates

[57] ABSTRACT

A radiation source for delivering a dose of radiation to a treatment site of a vessel is provided herein. The radiation source includes a delivery wire and a radioactive segment. The radioactive segment includes a substantially coiled or entwined radioactive wire which allows the radioactive segment to have a relatively large surface area to volume ratio. The delivery wire is made of material having a relatively short half-life, such as titanium, while the radioactive segment is made of a material, such as a rhenium or yttrium, which has a much longer half-life.

26 Claims, 4 Drawing Sheets

OTHER PUBLICATIONS

H. I. Amols, M. Zaider, J. Weinberger, R. Ennis, P. B. Schiff, and L. E. Reinstein. Dosimetric considerations for catheter–based beta and gamma emitters in the therapy of neointimal hyperplasia in human coronary arteries, *Int. J. Radiation Oncology Biol. Phys.*, vol. 36, No. 4, pp.: 913–921 (1996).

P. S. Teirstein, V. Massullo, S. Jani, J. J. Popma, G. S. Mintz, R. J. Russo, R. A. Schatz, E. M. Guarneri, S. Steuterman, N. B. Morris, M. B. Leon, and P. Tripuraneri. Catheter–Based Radiotherapy To Inhibit Restenosis After Coronary Stenting. *The New England Journal Of Medicine*, vol. 336, No. 24, pp. 1697–1703 (1997.

Y. Popowski, V. Verin, I. Papirov, P. Nouet, M. Rouzaud, E. Grob, M. Schwager, P. Urban, W. Rutishauser, and J. M. Kurtz. High Dose Rate Brachytherapy for Prevention of Restenosis after Percutaneous Transluminal Coronary Agnioplasty: Preliminary Dosimetric Tests of a New Source Presentation. *Int. J. Radiation. Oncology Biol. Phys.*, vol. 33, No. 1: 211–215 (1995).

Y. Popowski, V. Verin, I. Papirov, P. Nouet, M. Rouzaud, M. Schwager, P. Urban, W. Rutishauser, and J. M. Kurtz. Intra–Arterial Yttrium–90 Brachytherapy: Preliminary Dosimetric Study Using A Specially–Modified Angioplasty Balloon. *Int. J. Radiat. Oncol. Biol. Phys.*, 33: 713–717 (1995).

V. Verin, Y. Popowski, P. Urban, J. Belenger, M. Redard, M. Costa, M.C. Widmer, M. Rouzaud, P. Nouet, E. Grob, M. Schwager, J. M. Kurtz, and W. Rutishauser. Intra–Arterial Beta Irradiation Prevents Neointimal Hyperplasia In A Hypercholesterolemic Rabbit Restenosis Model. *Circulation*, vol. 92, No. 8: 2284–2290 (Oct. 15, 1995).

Y. Popowski, V. Verin, and P. Urban, Endovascular Beta–Irradiation After Percutaneuos Transluminal Coronary Balloon Angioplasty. *Int. J. Radiation Oncology Biol. Phys.*, vol. 36, No. 4, pp. 841–845 (1996).

V. Verin, P. Urban, Y. Popowski, M. Schwager, P. Nouet, P. A. Dorsaz, P. Chatelain, J. M. Kurtz, and W. Rutishauser, Feasibility of Interacoronary β–Irradiation to Reduce Restenosis after Baloon Angioplasty. A Clinical Pilot Study. *Circulation*, vol. 95, No. 5, pp. 1138–1144, Mar. 4, 1997.

Sandvik Rhenium Alloys, Pure Rhenium, Tungsten Rhenium and Molybdenum Rhenium Rod Technical Properties Data, P. O. Box, Elyria, Ohio 44036, Tel:216–365–7388.

RADIATION SOURCE WITH DELIVERY WIRE

FIELD OF THE INVENTION

The present invention relates generally to a device and method for treating a lesion or stenosis in a vessel of a patient. More specifically, the present invention relates to a radiation source which can be used with a catheter to deliver a dosage of radiation into a vessel to inhibit re-stenosis.

BACKGROUND OF THE INVENTION

It is well known that many medical complications are caused by the partial or total blockage of a blood vessel in a patient. Depending on the location of the particular blockage or stenosis, the patient can experience cardiac arrest, stroke, or necrosis of tissues or organs. Commonly, the stenosis results from plaque build-up in an artery. The plaque can vary in size and shape and can develop in different locations in a particular patient's cardiovascular system.

Several procedures have been developed to treat stenosis in the vessels of patients. For example, procedures such as angioplasty, stenting, incising and dilating, and atherectomy have been developed to treat stenosis in vessels. However, none of these procedures have been entirely successful in inhibiting or preventing the re-stenosis of a vessel after the procedure has been completed.

Recent studies have demonstrated the efficacy of radiation for inhibiting or preventing re-stenosis in a vessel by inhibiting or preventing the growth of fibrotic cells in the vessel wall, commonly referred to as neointima. In fact, devices have been developed for performing endovascular radiotherapy on a treatment site of a vessel to inhibit or prevent re-stenosis in the vessel. These devices commonly use a catheter to position a right, circular cylinder shaped radioactive segment in a vessel lumen of the vessel. The radioactive segment emits radiation until a prescribed dose of radiation has been delivered. However, the radioactive segment used with these devices has not been entirely satisfactory. For example, the radioactive segment has been unable to emit adequate amounts of radiation within the necessary short treatment times. Thus, it is often necessary to leave the radioactive segment in the vessel for an extended period of time in order to deliver a prescribed dose of radiation.

One attempt to solve this problem includes enlarging the diameter of the radioactive segment. This decreases the distance between the surface of the radioactive segment and the treatment area of the vessel, thus increasing the dose rate to the treatment area. However, enlarging the diameter of the radioactive segment limits these devices to relatively large and straight vessels. Furthermore, the enlarged diameter of the radioactive segment reduces blood flow in the vessel during treatment. This may cause potentially lethal complications.

An additional shortcoming of existing devices is the inflexibility of the right, circular cylinder shaped radioactive segment. In many instances, this inflexibility precludes treatment in small vessels and vessels having relatively sharp corners.

Further, existing devices include a radioactive segment which is typically made of a variety of different radioactive materials. However, these radioactive materials often emit complex and sometimes undesirable "contaminant radiation," thereby reducing the effectiveness of these radioactive materials. Accordingly, the radioactive segment is required to be encapsulated in another material to ensure that the radioactive contaminants are not released from the radioactive segment. This can add size and inflexibility to the radioactive segment. Furthermore, it also adds complexity to the design of the device and increases the cost of manufacturing the device. Moreover, many of these radioactive segments require excessively long activation times in the reactor to achieve suitable activity levels required for acceptable dose rates. Because of the low dose rates of the radioactive segments, excessively long treatment times are often necessary.

In light of the above, it is an object of the present invention to provide a device and method for quickly delivering a precise dose of radiation to a treatment site of a vessel. It is another object of the present invention to provide a device and method for delivering a dose of radiation to a treatment site of a relatively small and/or curved vessel. Still another object of the present invention is to provide a radiation source which is substantially disposable and is relatively inexpensive. Still another object of the present invention is to provide a device which is relatively safe and easy to manufacture and/or assemble. Yet another object of the present invention is to provide a radiation source that may be used without encapsulating or coating, may be used in an open ended catheter and may directly contact the patient's blood. Still another object of the present invention is to provide a way to quickly and accurately position the radiation source within the patient.

SUMMARY

A radiation source includes a radioactive segment attached to a delivery wire, which delivers a dose of radiation to a treatment site in a vessel of a patient. As provided in detail below, the present invention is unique since the radioactive segment is suitable for use in relatively small diameter vessels that presently cannot be treated with existing radiation sources. Moreover, the radioactive segment is made from materials which can relatively easily be made radioactive.

The treatment site is typically a stenosis in the vessel. However, it is believed that the radiation source can be used to treat other medical conditions near the vessel. The dose of radiation is typically administered to inhibit re-stenosis immediately prior or after other vascular procedures, such as angioplasty, stenting, incising and dilating, and/or atherectormy have been used for treatment of the stenosis. Alternately, the radiation source can be used instead of those procedures to treat the stenosis.

The radiation source is typically used with a delivery device positioned in the vessel of the patient. Typically, the radioactive segment and a portion of the delivery wire are inserted into a delivery lumen of the delivery device to position the radioactive segment adjacent the treatment site. Subsequently, the delivery wire is moved until the radioactive segment is positioned adjacent the treatment site. The radiation source provided herein is extremely versatile and can be used in a variety of delivery devices including catheters and/or balloon angioplasty catheters which are presently available.

The radioactive segment may be a bent radioactive wire which is coil shaped or entwined. As provided herein, this shape can help optimize the dose delivery of the radioactive segment by maximizing the surface area to volume ratio of the radioactive segment. This enables a relatively small radioactive segment to emit a prescribed dose of radiation, in a relatively short period of time. Further, the relatively small radioactive segment allows the radiation source to be used in relatively small and/or curved vessels. Additionally, the coiled shaped or entwined radioactive wire is more flexible than a right, circular cylinder shaped radioactive segment. This facilitates insertion of the radiation source into vessels having relatively sharp corners.

Typically, the radioactive segment is made radioactive (activated) by exposing the radioactive segment to neutron bombardment. In order to minimize the cost of handling hazardous radioactive materials, the radioactive segment can be designed for quick attachment to the delivery wire after neutron activation. Preferably, the delivery wire includes a receiver which facilitates the quick attachment of the radioactive segment to the delivery wire. The receiver is typically a relatively small segment of the delivery wire which can be easily secured to the delivery wire.

As provided herein, the radioactive segment can be secured to the receiver prior to activation of the radioactive segment. In this embodiment, the radioactive segment and the receiver will be simultaneously neutron bombarded in the reactor. This will save space in the reactor since only the radioactive segment and the receiver will be placed in the reactor. Further, this will facilitate easy attachment of the radioactive segment to the delivery wire.

In order to minimize the radiation being emitted from the receiver during use of the radiation source in the patient, the receiver is preferably made of material having a relatively short half-life when compared to the half-life of the radioactive segment. Because the receiver has a short half-life, after the neutron bombardment, radiation from the receiver quickly diminishes to an insignificant level. As provided herein, the receiver and the delivery wire can be made of material having a half-life of less than about ten (10) minutes and more preferably less than about six (6) minutes. For example, titanium can be used for the receiver and the delivery wire.

In contrast, the radioactive segment is preferably made of material having a half-life of at least about ten (10) hours and less than approximately one hundred (100) hours. Rhenium or yttrium can be used for the radioactive segment. Because the radioactive segment has a half-life of less than approximately one hundred (100) hours, the radioactive segment is substantially disposable.

BRIEF DESCRIPTION OF THE DRAWINGS

The novel features of this invention, as well as the invention itself, both as to its structure and its operation will be best understood from the accompanying drawings, taken in conjunction with the accompanying description, in which.

DESCRIPTION

Figure 1:
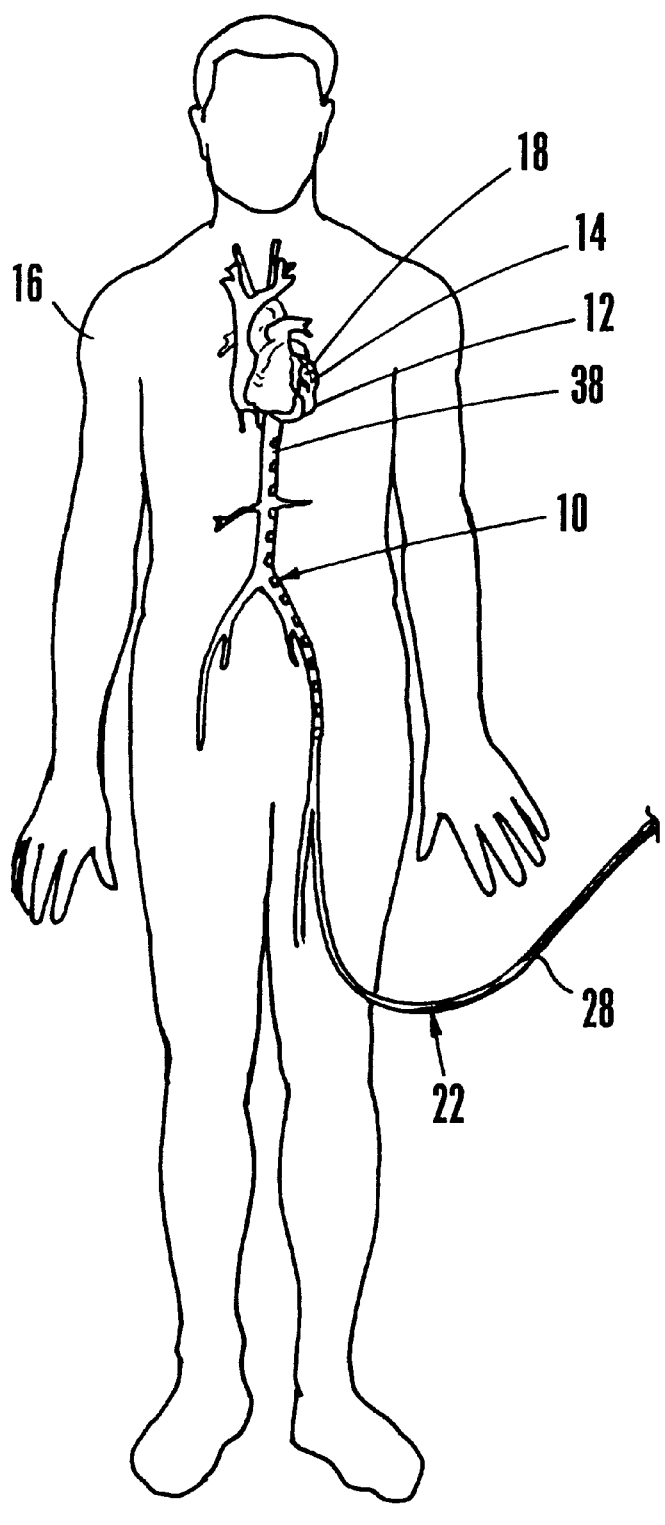
FIG. 1 is a plan view of a patient with a radiation source having features of the present invention positioned in a vessel of the patient.

Referring initially to FIG. 1, a radiation source 10 for delivering a dose of radiation to a treatment site 12 of a vessel 14 of a patient 16 is provided herein. The radiation source 10 is useful for treating a stenosis (not shown) in a vessel 14 in the vascular system of the patient 16 to prevent or inhibit the re-growth of neointima. The radiation source 10 is especially well suited for treating a stenosis in a coronary artery 18. However, it is anticipated that the present radiation source 10 can be used to treat other medical conditions.

Typically, the radiation source 10 will be used in conjunction with other vascular procedures, such as angioplasty, stenting, incising and dilating, and/or atherectomy, for the treatment of a stenosis in the vessel 14. However, the present device can also be used instead of those procedures.

The unique design of the radiation source 10, provided herein, allows the radiation source 10 to quickly emit a dose of radiation to the treatment site 12. Further, because of the unique design, the radiation source 10 can be used in relatively small, curved vessels 14. Additionally, the radiation source 10 is relatively easy to assemble and can be assembled after irradiation. Moreover, the portion of the radiation source 10 which is activated in the reactor is relatively small. Because of the small size, a number of radiation sources 10 can be simultaneously activated in a single reactor session. This will help reduce the cost of the radiation source and increase production.

A guiding catheter (not shown) is typically used with the delivery device 22 and the radiation source 10 for the treatment of coronary arteries 18. A suitable guiding catheter is sold by Medtronic of Minneapolis, Minn.

Figure 2:
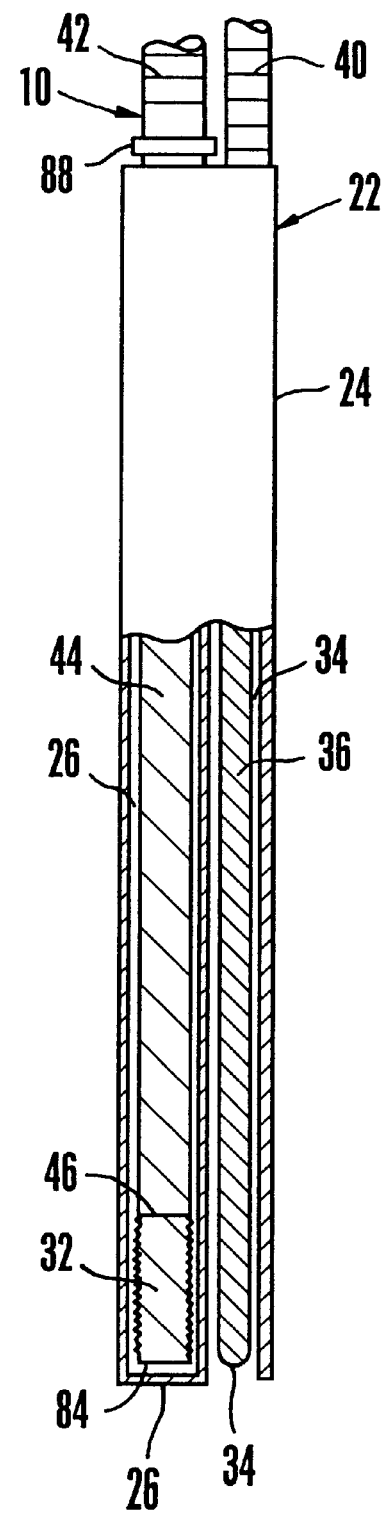
FIG. 2 is a side plan view in partial cut-away of a delivery device, a guide wire and a radiation source having features of the present invention.

A delivery device 22 is typically used to position the radiation source 10 in the vessel 14. FIG. 2 shows a delivery device 22 that can be used with the present invention. The delivery device 22 includes a catheter 24 having a delivery lumen 26, which is sized and shaped to receive a portion of the radiation source 10. The diameter of the delivery lumen 26 can be varied to suit the size of the radiation source 10. For example, in the embodiment shown in FIG. 2, the delivery lumen 26 has an inner diameter of between about one-half millimeter (0.50 mm) to three and one-half millimeters (3.50 mm).

As shown in FIG. 1, the delivery device 22 can include a substantially flexible shield 28 which encircles the portion of the catheter 24 which is outside the patient 16. The flexible shield 28 protects the medical staff during the positioning of the radiation source 10 in the patient 16. In the embodiment shown in FIG. 1, the flexible shield 28 is tubular and can be made from a number of materials including, for example, metallic foils of gold or lead, rubber and/or a combination thereof.

To deliver a dose of radiation, the delivery device 22 is inserted into the vessel 14, and a portion of the radiation source 10 is inserted into the delivery lumen 26 of the catheter 24. The delivery device 22 can be introduced into the vessel 14 wherever it is convenient.

Referring again to FIG. 2, the catheter 24 also includes a guide wire lumen 34 which is sized and shaped to receive a guide wire 36. The guide wire 36 inserts into a vessel lumen 38 of the vessel 14 and guides the catheter 24 through the vessel lumen 38 to the treatment site 12. A guide wire 36 having a diameter of about 0.35 millimeters, is acceptable.

Further, referring to FIG. 2, a distal end 84 of the delivery lumen 26 is enclosed while the guide wire lumen 34 is open.

Figure 3:
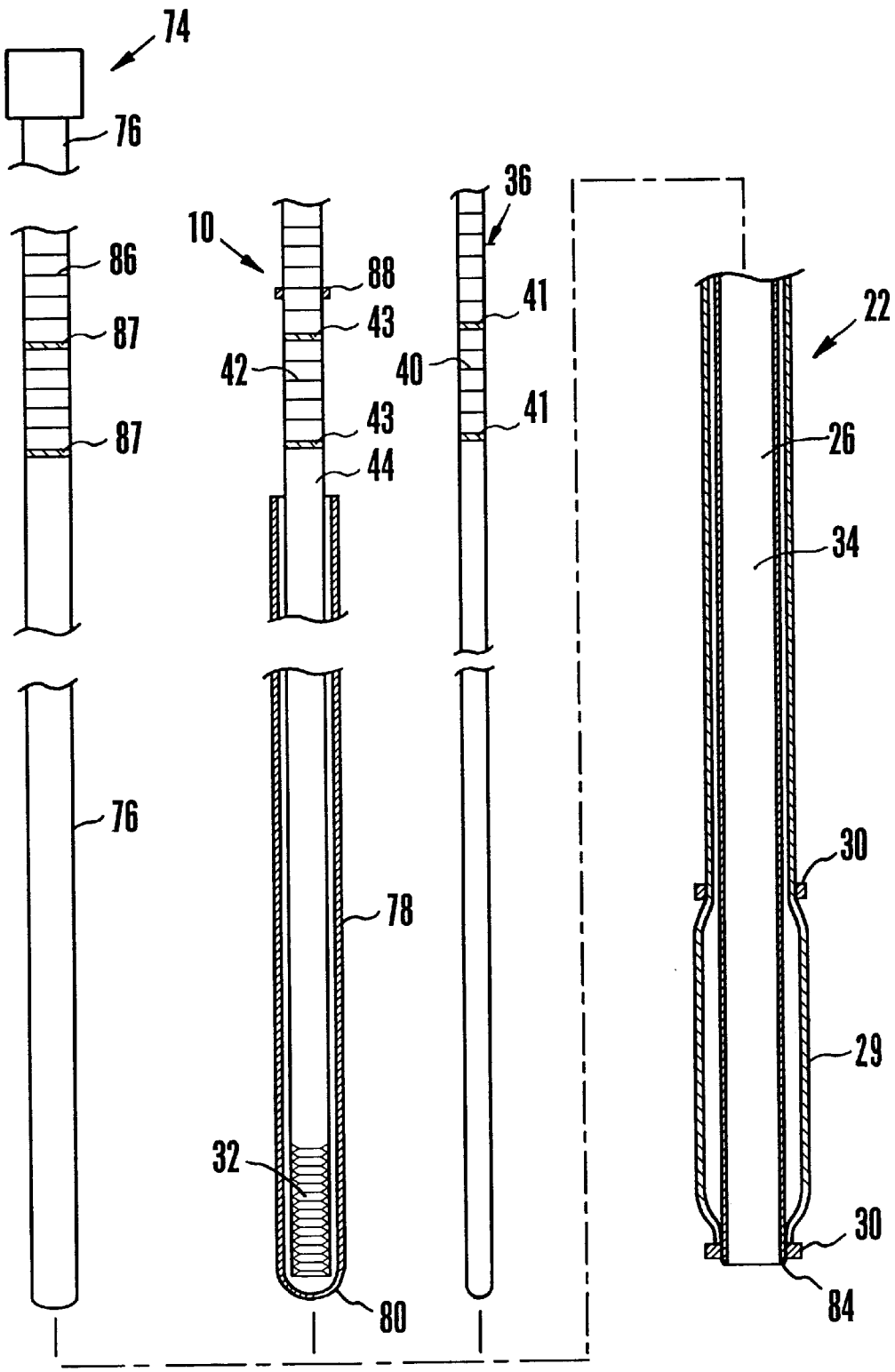
FIG. 3 is an exploded, partial cut-away view of a second delivery device, a guide wire, a radiation source, a sheath, and imaging systems having features of the present invention the present invention.

Preferably, the guide wire 36 includes a plurality of guide markers 40 positioned on the guide wire 36. The guide markers 40 assist in indicating the position of the guide wire 36 relative to the treatment site 12. The guide markers 40 can be implemented in a number of alternate ways. For example, the guide markers 40 can be painted marks or notches which are spaced apart on the guide wire 36. Further, as shown in FIG. 3, some of the guide markers 40 can be color coded guide markers 41 so that the position of the guide wire 36 in the vessel 14 can be quickly determined. For example, some of the color coded guide markers 41 can be green and some of the color coded guide markers 41 can be red. The guide markers 40 are typically positioned near the proximal end of the guide wire 36.

Importantly, as shown in FIG. 3, the delivery device 22 can alternately be an open ended balloon catheter having only a single lumen which functions as the guide wire lumen 34 and the delivery lumen 26. In this embodiment, the single lumen initially receives the guide wire 36 to position the delivery device 22. Subsequently, after the delivery device 22 is properly positioned, the guide wire 36 is removed and the radiation source 10 is inserted. Additionally, in this embodiment, the delivery device 22 includes a selectively inflatable balloon 29 for performing an angioplasty on the patient 16 and/or delivering a stent (not shown). Further, referring to FIG. 3, a distal end 84 of the delivery device 22 can be open.

Moreover, in this embodiment shown in FIG. 3, the delivery device 22 can include indicators 30 on the delivery device to assist in positioning the delivery device 22. The indicators 30 can each be a radiopaque band which is visible with a fluoroscope.

Suitable delivery devices 22 include a wide variety of different catheters which are currently used for other endovascular procedures. Open-ended, as well as closed-ended catheters that are presently available can be used with the present radiation source 10. Further, a single lumen or double lumen catheter can be used. Alternately, a delivery device 22 described in detail in U.S. patent application Ser. No. 08/827,489, entitled "An Intravascular Radiation Delivery Device," and assigned to the assignee of the present invention can be used with the present invention. The contents of U.S. patent application Ser. No. 08/827,489 are incorporated herein by reference.

Figure 4:
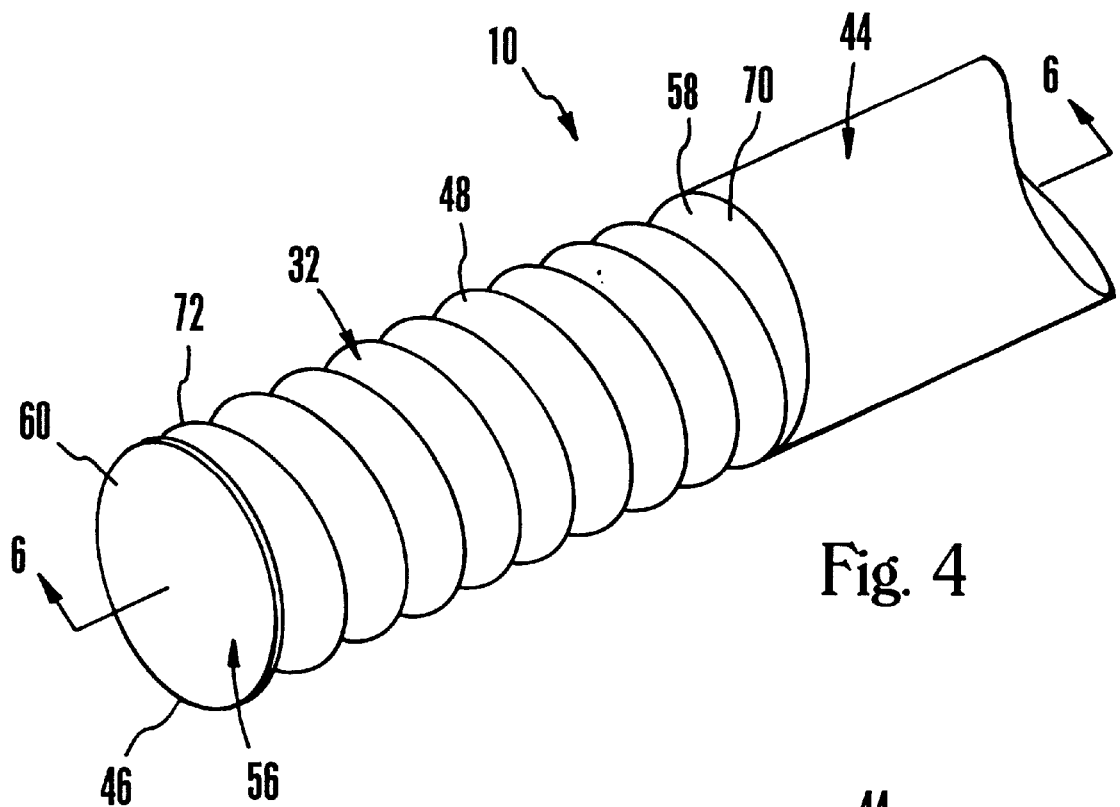
FIG. 4 is a perspective view of a first embodiment of a radiation source having features of the present invention.

Referring to FIG. 4, the radiation source 10 includes a delivery wire 44 and a radioactive segment 32. Importantly, the size of the radiation segment 32 can be varied to fit a variety of alternate sized delivery devices 22 which are appropriate for different sized vessels 14. Thus, the optimum size of radiation segment 32 can be used for each specific application. Because the radiation segment 32 provided herein is relatively inexpensive to manufacture, single usage radiation segments 32 can be custom made to suit the specific needs of a specific patient 16 and/or a variety of alternate sized radiation segments 32 can be provided to the hospital so that the doctor will be able to choose the radiation segment 32 which is appropriate for the specific patient.

The delivery wire 44 is used for positioning the radioactive segment 32 inside the delivery lumen 26 proximate the treatment site 12 of the vessel 14. The delivery wire 44 is flexible and sized to permit movement within the delivery lumen 26. Typically, the delivery wire 44 has a diameter of between about two-fifths of a millimeter (0.4 mm) and about three millimeters (3.0 mm).

The delivery wire 44 must be long enough to position the radioactive segment 32 adjacent the treatment site 12 in the vessel 14. The length of the delivery wire 44 varies according to the location of the stenosis in the vessel 14. Typically, the delivery wire 44 has a length of between about one and one-half meters (1.5 m) and two meters (2.0 m), although lengths outside of this range may occasionally be useful.

Accurate positioning can be obtained by directly viewing the radioactive segment 32 with a fluoroscope (not shown) and/or by utilizing a plurality of wire markers 42 which are positioned directly on the delivery wire 44. The wire markers 42 assist in indicating the position of the delivery wire 44 relative to the treatment site 12. The wire markers 42 can be implemented in a number of alternate ways. For example, the wire markers 42 can be painted marks or notches which are spaced apart on the delivery wire 44. Further, the wire markers 42 can include color coded wire markers 43 so that the position of the delivery wire 44 in the vessel 14 can be quickly determined. For example, some of the color coded wire markers 43 can be green, while other color coded wire markers 42 are other colors such as red or blue. The wire markers 42 are typically positioned near the proximal end of the delivery wire 44.

Preferably, as can best be seen in FIG. 3, the spacing and/or color coding of the wire markers 42 and color coded wire markers 43 correspond to spacing and/or color coding of the guide markers 40 and the color coded guide markers 41 so that the delivery wire 44 can be quickly and accurately positioned in the vessel 14.

A unique feature of the present invention is that the radioactive segment 32 can include a radioactive wire 48 with a plurality of bends. Utilizing a radioactive wire 48, which has the plurality of bends, increases the surface area to volume ratio of the radioactive segment 32. This enhances the emittance rate of radiation from the radioactive segment 32. Thus, a relatively small radioactive segment 32 can quickly deliver a dose of radiation to the treatment site 12 of the vessel 14. Additionally, the plurality of bends of the radioactive wire 48 enables the radiation segment 32 to be flexible. This enhances movement of the radioactive segment 32 within the delivery lumen 26 and allows the radiation source 10 to fit into smaller, curved vessels 14, than presently achievable with prior art systems.

The size and shape of the radioactive segment 32 may be adapted to suit the needs of the patient 16. The smaller size of the radioactive segment 32 allows the radiation source 10 to fit into smaller vessels 14 and vessels 14 having relatively sharp corners. Typically, the radioactive segment 32 is between approximately two centimeters (2.0 cm) to four centimeters (4.0 cm) in length and has an overall diameter of between approximately four-tenths of a millimeter (0.4 mm) to three millimeters (3.0 mm), although diameters outside this range can be used. Importantly, the diameter and length of the radioactive segment 32 may be increased or decreased to suit the specific needs of the patient 16.

In the embodiment shown in FIG. 4, the radioactive wire 48 is coil shaped. Utilizing the coil shaped radioactive wire 48 increases the surface area and enhances the flexibility of the radioactive segment 32. In this embodiment, the coil shaped radioactive wire 48 has a circular cross-section with a diameter of between about 0.05 millimeters and 0.2 millimeters. Those skilled in the art will recognize that other cross-sections, for example, hexagonal shaped cross-sections, may be used and that the diameter may be increased or decreased to suit the specific needs of the patient 16.

Figure 5:
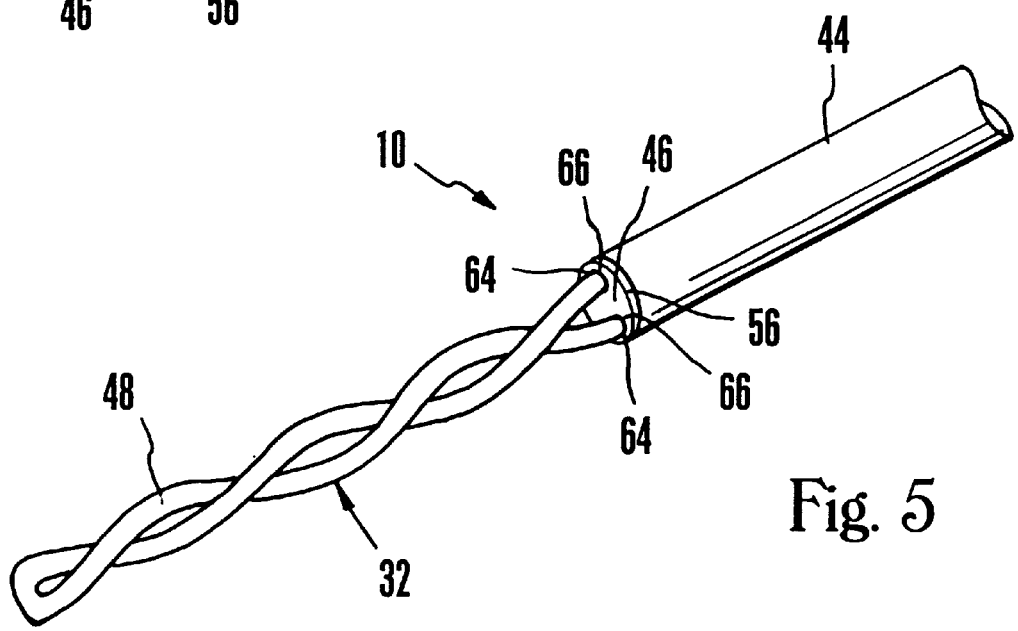
FIG. 5 is a perspective view of a second embodiment of a radiation source having features of the present invention.

Referring to FIG. 5, an alternative embodiment of the radiation source 10 is shown in which the radioactive wire 48 is entwined. Similarly, the entwined radioactive wire 48 increases the surface area to volume ratio of the radioactive segment 32 and enhances the flexibility of the radioactive segment 32. In this embodiment, the entwined radioactive wire 48 has a circular cross-section. Further, as an alternative to entwining the radioactive wire 48, the radioactive wire 48 may be braided (not shown) or woven (not shown).

Figure 6:
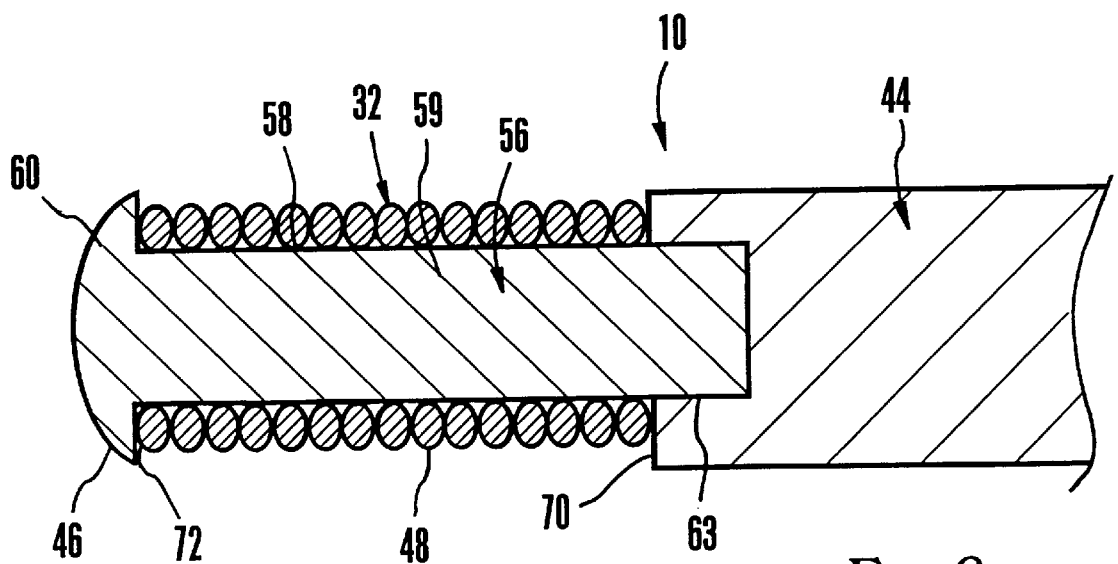
FIG. 6 is a cross-sectional view taken on line 6—6 in FIG. 4.

The radioactive segment 32 can be secured to the delivery wire 44 in a number of alternate ways. As provided herein, the radioactive segment 32 is typically made radioactive (activated) by exposing the radioactive segment 32 to neutron bombardment. In order to minimize the cost of handling hazardous radioactive materials, the radioactive segment 32 can be designed for quick attachment to the delivery wire after neutron activation. Referring to FIGS. 4–6, the delivery wire 44 can include a receiver 56, for quickly and easily securing the radioactive segment 32 to the delivery wire 44. In these embodiments, the receiver 56 is typically a relatively small segment of the delivery wire 44 which can be easily secured to the delivery wire 44. Further, in some embodiments, the receiver 56 can support the radioactive segment 32 during fabrication and activation.

In the embodiment, shown in FIGS. 4 and 6, the receiver 56 is pin shaped and includes a right, circular, cylinder shaped receiver body 59 for receiving the radioactive segment 32 and a receiver head 60 for retaining the radioactive segment 32. As can best be seen in FIG. 6, the delivery wire 44 can include a delivery aperture 63, to facilitate attachment of the receiver 56 to the rest of the delivery wire 44. In this embodiment, the receiver body 59 inserts into the delivery wire aperture 63 and may be welded or otherwise secured, to the rest of the delivery wire 44 after positioning the radioactive segment 32 on the receiver 56.

Figure 7:
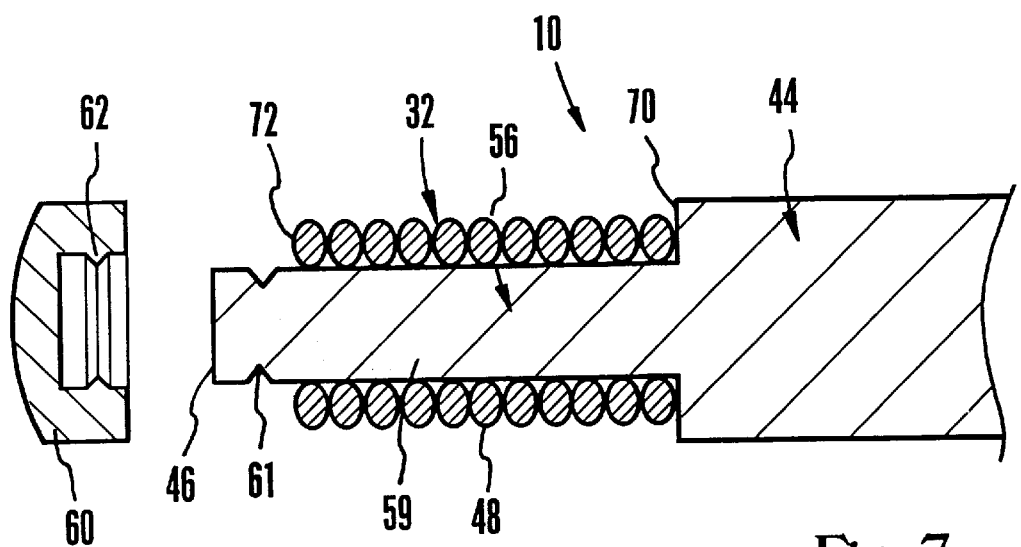
FIG. 7 is a cross-sectional view of an embodiment of a radiation source having features of the present invention.

An alternative embodiment is shown in FIG. 7. In this embodiment, a portion of the receiver 56, namely, the receiver body 59 is an integral part of the delivery wire 44 and the receiver head 60 is selectively attachable to the receiver body 59. Use of the selectively attachable receiver head 60 facilitates installation of the radioactive segment 32 onto the delivery wire 44 and removal of the radioactive segment 32 for cleaning, replacement, or reactivation of the radioactive segment 32.

The selectively attachable receiver head 60 may be secured to the delivery wire 44 in a variety of ways. For example, as shown in FIG. 7, a compressible ring 62 which fits into a circumferential groove 61 in the receiver body 59 may be used. Alternately, threads (not shown), a weld (not shown), or other types of fasteners may be used. In still another embodiment (not shown), the receiver head 60 can be crimp fitted to the receiver body 59.

If desired, the receiver body 59 may be shaped differently than that shown in FIGS. 4, 6, and 7. For example, the receiver body 59 may be tapered. Additionally, the receiver head 60 may be shaped similar to a hemisphere or a portion of an ellipsoid.

In the embodiment shown in FIG. 5, the radioactive segment 32 is secured to the delivery wire 44 differently than in the embodiments shown in FIGS. 4, 6, and 7. In the embodiment shown in FIG. 5, two (2) wire ends 64 of the entwined radioactive wire 48 affix to holes 66 formed in the receiver 56. In this embodiment, the receiver 56 is disk shaped and is secured to the rest of the delivery wire 44 with a weld, an adhesive, or some other method.

Activation of the radioactive segment 32 after attachment to the receiver 56 may simplify the assembly of the radioactive segment 32 to the delivery wire 44. Preferably, the receiver 56 is made from a material having a half-life much shorter than the half-life of the radioactive segment 32. This will allow for the radioactivity of the receiver 56 to diminish relatively quickly after neutron bombardment. Further, this permits activation and reactivation of the radioactive segment 32 with the radioactive segment 32 attached to the receiver 56. For ease of manufacturing, the delivery wire 44 is typically made from the same material as the receiver 56.

A suitable delivery wire 44 and receiver 56 are made of material having a half-life of less than about ten (10) times and more preferably less than one hundred (100) times the half-life of the radioactive segment 32. The delivery wire 44 and the receiver 56 can have a half-life of about ten (10) minutes and preferably less than about six (6) minutes. For example, titanium, which has a half-life of approximately six (6) minutes can be utilized. Other suitable materials can include aluminum, magnesium or stainless steel.

Preferably, the radioactive segment 32 emits $\beta$ particles, since $\beta$ particles have a relatively short tissue penetration level. Because of the short tissue penetration of $\beta$ particles, the medical staff is exposed to less radiation. Preferably, the radioactive segment 32 also has a relatively high activity level so the prescribed dose of radiation emits quickly into the patient 16 and the treatment is administered in a relatively short period of time into the patient 16. For example, the radioactive segment 32 can include rhenium having an activity level of about two (2) mCi to 300 mCi and a suitable tissue penetration level of between about 1.0 mm and 3.0 mm.

In order to produce a radioactive segment 32 with the desired shape, flexibility, radioactivity, and half-life discussed above, the radioactive wire 48 must be made from an appropriate material. A suitable radioactive segment 32 can be made from rhenium.

Isotopes of rhenium (Re-185 and Re-187) can be directly activated in a reactor by neutron bombardment (producing Re-186 and Re-188). Enriched rhenium, in which a higher proportion of Re-187 is present, may also be used, thereby enhancing the proportion of Re-188 that is produced. Because rhenium has a good capture cross-section, even nuclear reactors having relatively low neutron fluxes can be used to activate the rhenium. This allows the radioactive segment 32 to be activated at numerous locations throughout the world. This can reduce the costs for activating and shipping the radioactive segment 32.

Further, with rhenium, the reactors can give suitable activity levels within a relatively short activation time, i.e., less than approximately five (5) hours. The result is the radioisotope Re-186 with a half-life of approximately ninety and six tenths (90.6) hours and the radioisotope Re-188 with a half-life of approximately seventeen (17.0) hours. Both radioisotopes are therapeutically useful $\beta$ emitters, which produce sufficiently high levels of radiation for treatment of vessels for approximately four (4) days after neutron activation of the radioactive segment 32. Further, because the rhenium is relatively inexpensive and has a relatively short half-life, i.e., less than approximately one hundred (100) hours, the radiation segment 32 is substantially disposable. As a result thereof, the radioactive segment 32 can be specifically sized and designed for a particular patient 16 and subsequently disposed of after usage on that patient 16.

The rhenium 186–188 combination also emits, in addition to the $\beta$ radiation, a small percentage of gamma radiation. This will assist in locating and detecting any radioactive segments 32, which may became lost during handling or use of the radioactive source. This improves safety of the radioactive segment 32. Further, rhenium is very dense and can therefore be easily and directly viewed with a fluoroscope to properly position the radioactive segment 32.

An alternate useful element for the radioactive segment 32 is yttrium. The naturally occurring metal Y-89 can be made radioactive by neutron bombardment to yield pure β-emitter Y-90. The Y-90 has dosimetric properties which are similar to the dosimetric properties of Re-188. However, the Y-90 has a half-life of approximately sixty-four (64.0) hours. This is longer than that of Re-188. This allows the radioactive segment 32 to be used for a longer period of time, i.e., up to eight (8) days after neutron activation of the radioactive segment 32. Another advantage of Yttrium-90 is that because it is a pure β-emitter it does not require any secondary gamma shielding or encapsulating. This will reduce the shielding necessary during transportation and handling.

However, the Y-90 has a lower capture cross-section for neutrons than the rhenium. This means that substantially higher neutron fluxes or long neutron activation times are necessary to produce the same activity Y-90 as would be produced with rhenium. This will limit the choice of reactors for activating the radioactive segment 32.

Further, yttrium is less dense than the rhenium. This may make a radioactive segment 32 made from yttrium more difficult to locate with fluoroscopy. Moreover, care must be taken that no ionic Y-90 is released from the radioactive segment 32, since it is preferentially absorbed by bone and can cause hematopoiotic toxicities.

In some instances, it may be desirable to minimize the emission of radiation to areas outside the treatment site 12. To accomplish this, radioactive blockers (not shown) made from materials that inhibit the passage of radiation can be located near the radioactive segment 32 to inhibit passage of radiation to areas outside of the treatment site 12. Such radioactive blockers may be positioned within or on the delivery device 22 to control the intensity of radiation to different parts of the vessel 14 and the patient 16.

Once the radioactive segment 32 is positioned inside the patient 16, the body of the patient 16 will shield the beta particles. However, an outside shield (not shown) may be used outside of the patient 16 to protect the medical staff from gamma rays from the radiation source 10. The outside shield can be implemented in a number of ways. For example, the outside shield can be an attachment to a table which can be positioned close to the patient 16. The outside shield can be made of lead which is enclosed by a steel jacket. Additional shielding materials (not shown) may be necessary when the radioactive segment 32 is outside the patient 16.

Referring again to FIG. 3, the radiation source 10 is preferably used with an imaging system 74, which provides an accurate and detailed map or image of the internal structure of the vessel 14. A suitable imaging system 74 is an Intravascular Ultrasound System ("IVUS System") sold by Boston Scientific. The imaging system 74 includes an imaging probe 76 which is inserted into the vessel lumen 38 or the delivery lumen 26 of the deliver device 22 to image the structure of the vessel 14.

Optionally, after the delivery device 22 has been inserted into the vessel lumen 38, the imaging system 74 may be used again to ensure proper positioning of the delivery device 22. Preferably, the imaging probe 76 includes probe markers 86 to assist in the correct placement of the radioactive segment 32 relative to the treatment site 12. The probe markers 86 can be implemented in a number of alternate ways. For example, the probe markers 86 can be painted marks or notches which are spaced apart on the imaging probe 76. Further, the probe markers 86 can include color coded probe markers 87 so that the position of the probe markers 86 in the vessel 14 can be quickly determined. The probe markers 86 are typically positioned near the proximal end of the imaging probe 76.

Preferably, as can best be seen in FIG. 3, the spacing and/or the color coding of the probe markers 86 and the color coded probe markers 87 correspond to spacing and/or color coding of the guide markers 40, the color coded guide markers 41, the wire markers 42 and the color coded wire markers 43 so that the delivery wire 44 can be quickly and accurately positioned in the vessel 14.

As shown in FIG. 3, a sheath 78 can be used to isolate the radiation source 10. If the distal end 84 of the delivery lumen 26 is open, the sheath 78 prevents direct contact between the blood (not shown) and the radioactive segment 32. This is necessary if a non-sterile radioactive segment 32 is used. The sheath 78 is typically tubular and includes a closed distal end 80. The sheath 78 covers the radioactive segment 32 to provide a barrier between the radiation segment 32 and the blood. The sheath 78 can be made of a thin, high density polyethylene or another suitable material.

Regulatory requirements may change in the near future to allow un-coated and unshielded radiation segments 32 to be used in inter-vascular applications. The radioactive segment 32 provided herein is designed with this in mind and offers the distinct advantage over other radioactive segments 32 with regards to stability and radiation energy.

Referring to FIG. 2, the distal end 84 of the delivery device 22 is closed and prevents the radioactive segment 32 from escaping into the vessel 14 and prevents direct contact between the blood (not shown) in the vessel 14 and the radiation source 10. In this embodiment, the use of the sheath 78 is optional.

A dummy rod (not shown) can be used for inserting the sheath 78 into the delivery lumen 26 and for insuring that the delivery lumen 26 is not collapsed. The dummy rod is designed to have substantially the same size, shape, and flexibility as the radiation source 10. Additionally, the dummy rod can include dummy markers (not shown) which can assist in the correct placement of the radioactive segment 32 proximate the treatment site 12. The dummy markers can be designed and utilized similar to the guide markers 40 described above. Basically, the dummy rod can be used to insure that the radiation source 10 will move smoothly within the delivery lumen 26.

OPERATION

An example of the operation of the radiation source 10 can best be visualized with initial reference to FIGS. 1 and 2. First, the guiding catheter (not shown) is inserted into the coronary artery 18 ostium. Next, the guide wire 36 is positioned in the vessel 14 of the patient 16. This is done to establish a mechanical pathway through the vessel 14 to the treatment site 12 where the radiation is to be released. Next, the imaging system 74 can be used to provide an accurate and detailed map or image of the internal structure of the vessel 14. With the information obtained from the imaging system 74, the location of the treatment site 12, and the size and shape of the stenosis is determined.

Next, a vascular procedure for treatment of a stenosis in the vessel 14, such as angioplasty, stenting, incising and dilating, and/or atherectomy can optionally be performed upon the vessel 14. The delivery device 22 shown in FIG. 3 can be used to perform some of these procedures. If an initial vascular procedure is performed on the vessel 14, the imaging probe 76 may be reinserted to provide an accurate and detailed map or image of the residual internal structure of the vessel 14.

Next, for the embodiment shown in FIG. 2, the guide wire lumen 34 of the delivery device 22 is moved over the guide wire 36 until a portion of the delivery device 22 is positioned adjacent the treatment site 12 in the vessel 14. Next, the radioactive segment 32 is installed into the delivery lumen 26.

Importantly, as shown in FIG. 2, the guide markers 40 on the guide wire 36 can be used in conjunction with the wire markers 42 on the delivery wire 44 to properly position the radioactive segment 32 in the delivery device 22. Further, a stop 88, e.g., a clamping device or small "O" ring can be positioned on the delivery wire 44 so that the physician is able to easily determine when the radioactive segment 32 is properly positioned. Subsequently, the positioning of the radioactive segment 32 can be confirmed with a fluoroscope.

Alternately, for the embodiment shown in FIG. 3, after the delivery device 22 has been inserted into the vessel, the guide wire 36 may be removed and the radioactive segment 32 advanced through the delivery device 22 to the treatment site 12. Optionally, in the embodiment shown in FIG. 3, after the delivery device 22 has been inserted into the vessel lumen 38, the guide wire 36 can be removed and the imaging probe 76 of the imaging system 74 inserted into the delivery lumen 26 to ensure proper positioning of the catheter 24. The image is analyzed and the catheter 24 is repositioned if necessary. The imaging probe 76 is then removed from the delivery lumen 26.

Next, for the embodiment shown in FIG. 3, the sheath 78 can be positioned over the radioactive segment 32 and the radioactive segment 32 installed into the delivery lumen 26. The sheath 78 protects and contains the radiation source 10. The radioactive segment 32 and the sheath 78 are inserted into the delivery device 22 until the radioactive segment 32 is positioned adjacent the treatment site 12. Alternately, the sheath 78 may be installed into the delivery lumen 26 with the dummy rod prior to the inserting the radioactive segment 32.

Importantly, in this embodiment, the probe markers 86 on the imaging probe 76 or the guide markers 40 on the guide wire 36 can be used in conjunction with the wire markers 42 on the delivery wire 44 to properly position the radioactive segment 32 in the delivery device 22. The stop 88 can be positioned on the delivery wire 44 so that the physician is able to easily determine when the radioactive segment 32 is properly positioned. Subsequently, the positioning of the radioactive segment 32 can be confirmed with a fluoroscope.

The radioactive segment 32 remains positioned in the delivery area 30 and is allowed to emit radiation until the proposed dose is released. The amount of time required to give the correct amount of dose can be obtained from a calibration sheet (not shown) supplied with each radiation source 10. The calibration sheet can include the time for the radioactive segment 32 to remain adjacent to the treatment site 12 for a particular dose to be delivered at a particular distance, i.e., typically between one millimeter (1.0 mm) to three millimeters (3.0 mm) from the center of the radioactive segment 32. The physician will determine the necessary treatment depth for each individual patient using the imaging system 74 or other imaging procedures. The calibration sheet can account for decay of the radioactive segment 32 by giving appropriate times for treatments to the nearest one-half (0.50) hour during the day.

Subsequently, the radiation source 10 is removed from the delivery lumen 26 and stored in a shielded container (not shown) for safe storage and transport. The delivery device 22 is then removed from the vessel lumen 38.

While the particular radiation source 10 for delivering a dose of radiation to a treatment site 12 of a vessel 14, as herein shown and disclosed in detail, is fully capable of obtaining the objects and providing the advantages herein before stated, it is to be understood that it is merely illustrative of the presently preferred embodiments of the invention and that no limitations are intended to the details of the construction or design herein shown other than as defined in the appended claims.

What is claimed is:

1. A radiation source adapted for use with a delivery device for delivering a dosage of radiation to a treatment site of a vessel, the delivery device being adapted to be inserted into the vessel and including a delivery lumen, the radiation source comprising:

a radioactive segment including a radioactive wire having a plurality of tightly packed adjacent coils, wherein adjacent coils are in contact along substantially the entire radioactive segment; and a delivery wire which is adapted to be inserted into the delivery lumen with the delivery device inserted into the vessel, the delivery wire including a receiver securing the radioactive segment to the delivery wire, the receiver having a receiver body and a receiver head, the receiver body having a distal end and being positioned within and substantially through the radioactive segment, and the receiver head being selectively attached to the distal end of the receiver body to secure the radioactive segment to the receiver body.

2. The radiation source of claim 1 wherein the radioactive segment includes rhenium.

3. The radiation source of claim 1 wherein the radioactive segment has a half-life of less than approximately one hundred (100) hours.

4. The radiation source of claim 1 further comprising a sheath which substantially encircles the radioactive segment and is adapted to fit over the radioactive segment in the delivery lumen.

5. A radiation source for use with a delivery device for delivering a dose of radiation to a treatment site of a vessel, the delivery device adapted for being inserted into the vessel and including a delivery lumen, the radiation source comprising:

a delivery wire which is adapted for being inserted into the delivery lumen after the delivery device is inserted into the vessel; and a radioactive segment secured to the delivery wire, the radioactive segment including a material which emits beta rays and a small amount of gamma rays.

6. The radiation source of claim 1 wherein radioactive segment is made of a material which emits beta radiation and a small amount of gamma radiation to facilitate locating the radioactive segment.

7. The radiation source of claim 1 wherein the delivery wire includes wire markers positioned near a proximal end of the delivery wire, the wire markers being useful for positioning the radioactive segment in the vessel.

8. The radiation source of claim 7, wherein the wire markers are color coded.

9. The radiation source of claim 1 including a stop secured to the delivery wire near a proximal end of the delivery wire, the stop being useful for positioning the radioactive segment in the vessel.

10. The radiation source of claim 5, wherein the delivery wire includes a receiver for securing the radioactive segment to the delivery wire, the receiver having a receiver body and a receiver head, the receiver body being positioned within the radioactive segment, and the receiver head being selectively attached to a distal end of the receiver body to secure the radioactive segment to the receiver body.

11. The radiation source of claim 5, wherein the delivery wire includes wire markers positioned near a proximal end of the delivery wire, the wire markers being useful for positioning the radioactive segment in the vessel.

12. The radiation source of claim 5, including a stop secured to the delivery wire near a proximal end of the delivery wire, the stop being useful for positioning the radioactive segment in the vessel.

13. A radiation source adapted for use with a delivery device for delivering a dosage of radiation to a treatment site of a vessel, the delivery device being adapted to be inserted into the vessel, the delivery device including a delivery lumen, the radiation source comprising:

a radioactive segment including a longitudinally extending opening;

a delivery wire which is adapted to be inserted into the delivery lumen with the delivery device inserted into the vessel, the delivery wire including a receiver body positioned within the opening of the radioactive segment, the receiver body including a distal end; and a receiver head attached to the distal end of the receiver body to secure the radioactive segment on the receiver body.

14. The radiation source of claim 13, wherein the receiver body extends substantially through radioactive segment and includes a circumferential groove located near the distal end of the receiver body and the receiver head includes a tubular ring which engages the circumferential groove to attach the receive head to the receiver body.

15. The radiation source of claim 13 wherein the delivery wire includes wire markers positioned near a proximal end of the delivery wire, the wire markers being adapted for positioning the radioactive segment in the vessel.

16. A radiation source adapted for use with a delivery device for delivering a dosage of radiation to a treatment site of a vessel, the delivery device being adapted to be inserted into the vessel, the delivery device including a delivery lumen, the radiation source comprising:

a radioactive segment including a longitudinally extending opening;

a delivery wire which is adapted to be inserted into the delivery lumen with the delivery device inserted into the vessel, the delivery wire including a delivery wire aperture positioned near a distal end of the delivery wire; and a receiver securing the radioactive segment to the delivery wire, the receiver having a receiver body and a receiver head secured to a distal end of the receiver body, the receiver body being positioned within the opening of the radioactive segment with a proximal end of the receiver body positioned within the delivery wire aperture to secure the radioactive segment to the receiver body.

17. The radiation source of claim 16, wherein the radioactive segment includes a radioactive wire having a plurality of tightly packed adjacent coils and the radioactive segment is made of a material which emits beta radiation and a small amount of gamma radiation to facilitate locating the radioactive segment.

18. The radiation source of claim 16, wherein the delivery wire includes wire markers positioned near a proximal end of the delivery wire, the wire markers being adapted for positioning the radioactive segment in the vessel.

19. A radiation source, comprising:

a radioactive segment;

a delivery wire having a delivery wire aperture; and a receiver having a receiver body and a portion of the receiver body is inserted into the delivery wire aperture in order to attach the radioactive segment to the delivery wire.

20. A radiation source as defined in claim 19, wherein the receiver is pin shaped.

21. A radiation source as defined in claim 19, wherein the receiver is made from a material that has a shorter half-life than that of the radioactive segment.

22. A radiation source as defined in claim 19, wherein the receiver body is positioned within an opening in the radioactive segment.

23. A radiation source, comprising:

a radioactive segment;

a delivery wire having a receiver body for receiving the radioactive segment; and a receiver head which attaches to the receiver body and secures the radioactive segment to the delivery wire.

24. A radiation source as defined in claim 23, wherein the receiver body is a portion of the delivery wire which has a reduced diameter.

25. A radiation source as defined in claim 23, wherein the receiver head is selectively attachable to the receiver body allowing for quick attachment and removal of the radioactive segment from the delivery wire.

26. A radiation source as defined in claim 23, wherein the receiver body is positioned in an opening in the radioactive segment.

\* \* \* \* \*